United States Patent
Kellenberger et al.

(10) Patent No.: US 10,221,206 B2
(45) Date of Patent: *Mar. 5, 2019

(54) SELECTED MACROLIDES WITH PDE4-INHIBITING ACTIVITY

(71) Applicant: Basilea Pharmaceutica AG, Basel (CH)

(72) Inventors: Johannes Laurenz Kellenberger, Riehen (CH); Jürg Dreier, Witterswil (CH)

(73) Assignee: Basilea Pharmaceutica AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/667,894

(22) Filed: Aug. 3, 2017

(65) Prior Publication Data

US 2017/0327525 A1    Nov. 16, 2017

Related U.S. Application Data

(63) Continuation of application No. 14/653,928, filed as application No. PCT/EP2013/078040 on Dec. 27, 2013, now Pat. No. 9,738,676.

(30) Foreign Application Priority Data

Dec. 31, 2012 (EP) ..................... 12199801
Mar. 12, 2013 (EP) ..................... 13158812

(51) Int. Cl.
*C07H 17/08* (2006.01)

(52) U.S. Cl.
CPC .................. *C07H 17/08* (2013.01)

(58) Field of Classification Search
CPC .................................. C07H 17/08
See application file for complete search history.

(56) References Cited

U.S. PATENT DOCUMENTS

| 7,524,823 B2 * | 4/2009 | Kellenberger ......... C07H 17/08 514/29 |
| 2011/0021449 A1 * | 1/2011 | Kellenberger ..... A61K 31/7048 514/29 |

* cited by examiner

*Primary Examiner* — Jonathan S Lau

(57) ABSTRACT

The application relates to the macrolide compound of the formula (I):

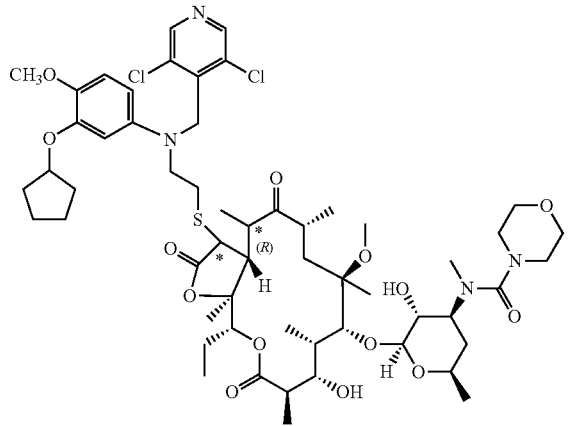

wherein
* indicates a stereocentre which is in (R) or (S) configuration,
or a pharmaceutically acceptable salt or ester thereof.

2 Claims, No Drawings

SELECTED MACROLIDES WITH PDE4-INHIBITING ACTIVITY

This application is a domestic application, filed 3 Aug. 2017; and claims benefit as a CON of Ser. No. 14/653,928 filed 19 Jun. 2015, issued as U.S. Pat. No. 9,738,676, which is a 371 of PCT/EP2013/078040 filed 27 Dec. 2013; claims benefit of foreign priority document EPO 12199801.7, filed 31 Dec. 2012; and claims benefit of foreign priority document EPO 13158812.1, filed 12 Mar. 2013; the foreign priority documents are in English.

The invention relates to a novel macrolide compound, the use of said compound as medicament, in particular for the treatment or prevention of inflammatory and allergic diseases, pharmaceutical compositions containing said compound and to a process for its preparation. The invention relates in particular to a macrolide compound with anti-inflammatory activity mediated primarily through inhibition of phosphodiesterase 4 (PDE4) which makes it useful for the treatment and/or prevention of inflammatory and allergic diseases such as chronic obstructive pulmonary disease (COPD), asthma, rheumatoid arthritis, atopic dermatitis, psoriasis or inflammatory bowel disease or proliferative diseases such as cancer.

Cyclic adenosine monophosphate (cAMP) is a key second messenger in cells. Increased levels of cyclic AMP are known to suppress pro-inflammatory responses in various types of inflammatory and immune cells including lymphocytes, monocytes, macrophages, neutrophils, eosinophils, basophils and lung epithelial cells. Intracellular concentrations of cAMP are regulated by adenylyl cyclase and by cyclic nucleotide phosphodiesterases (PDEs). PDEs are a family of enzymes that inactivate cyclic nucleotides cAMP and cGMP through hydrolysis to AMP and GMP. The cAMP-specific enzyme PDE4 is ubiquitous in inflammatory and immune cells. PDE4 has been shown to be involved in inflammatory processes (cf. e.g. Lipworth B. J., Lancet (2005) 365, p. 167; Houslay M. D. et al. Drug Discovery Today (2005) 10 (22), p 1503; Halpin D. M. G. Int. J. COPD (2008) 3(4), p. 543, or Sanz M. J. et al. Pharmacology & Therapeutics (2005) 106, p. 269). Therefore, inhibitors of PDE4 are useful in the treatment and/or prophylaxis of inflammatory and allergic diseases such as asthma, chronic bronchitis, emphysema, atopic dermatitis, urticaria, allergic rhinitis, allergic conjunctivitis, psoriasis, rheumatoid arthritis, chronic obstructive pulmonary disease (COPD), septic shock, ulcerative colitis, Crohn's disease, adult respiratory distress syndrome and multiple sclerosis. PDE4 inhibitors are also useful for the treatment of proliferative diseases such as human cancer (cf e.g. Cancer Research, 2007, 67, p. 5248).

Numerous PDE4 inhibitors have been disclosed in the literature. (see for example J. O. Odingo, Expert. Opin. Ther. Patents, 2005, 15(7), 773; M. Hendrix, C. Kallus, Methods and Principles in Medicinal Chemistry (2004), Vol. 22 (Chemogenomics in Drug Discovery), 243-288 (Wiley-VCH)). Many of the known PDE4 inhibitors show dose-limiting side-effects such as emesis and headache.

Erythromycin derivatives having a five-membered lactone ring fused to the 11,12-positions of the macrolactone ring have been disclosed in e.g. WO 02/16380, WO 03/004509, WO 03/042228, WO 03/072588, WO 03/024986, US 2004/0038915 and in WO2005067919. Documents WO 02/16380, WO 03/072588, WO 03/024986 and US 2004/0038915 describe exclusively so-called ketolides having a carbonyl group at position 3 of the erythromycin scaffold. WO 03/042228, WO 03/004509 and WO2005/067919 disclose macrolide derivatives with a 11,12 lactone ring fused to the 11,12-positions and a cladinose sugar substituent at position 3 of the erythromycin scaffold.

Erythromycin derivatives with a double bond at positions 2,3 of the erythromycin scaffold, so-called anhydrolides, have been disclosed e.g. in WO97/42205 and U.S. Pat. No. 6,720,308. Compounds with a hydroxyl group in position 3 of the erythromycin scaffold are found as intermediates in the synthesis of various compounds mentioned above and are also disclosed in e.g. WO2004/013153. Formation of 3-acyl-derivatives is described in e.g. *J. Med. Chem.* 2003, 46, 2706.

Oral administration of drugs is generally considered to be the most convenient and most popular way for administration of a drug. Oral bioavailability of a drug is accordingly a very important pharmacological parameter of a drug. The oral bioavailability of macrolides differs strongly and is frequently rather poor.

A frequently encountered problem in drug development and also for marketed drugs are cardiovascular side effects. In many cases, these effects are due to a compound induced prolongation of the QT interval in the electrocardiogram (ECG), which is associated with potentially fatal arrhythmia or "torsades des pointes". Several anti-infective agents like macrolides, ketolides and fluoroquinolones have been associated with QT prolongation.

The QT interval is a measure of the duration of ventricular depolarization and repolarization involving several membrane ion channels and transporters. In many cases, the inhibition of the delayed rectifier $K^+$ current (IKr), which involves the human Ether-a-go-go Related Gene (hERG) potassium channel, has been linked to drug induced QT prolongation. Inhibition of the hERG channel is therefore used to predict the risk of compound induced QT prolongation.

Most of the molecules described in the references cited above have substantial anti-infective activity. However, if erythromycin derivatives are foreseen for chronic treatment of diseases not caused by pathogenic bacteria, it is desirable to have compounds devoid of anti-infective activity in order to avoid the development of antibiotic-resistant bacteria. It has been reported that modifications of the desosamine moiety can lead to a loss of antibacterial activity. Various modifications of the desosamine sugar moiety of erythromycin derivatives have been described in the literature as exemplified by the following publications: WO2007/129646, WO2004/013153 and Bioorg. Med. Chem. 2007, 15, 3266.

WO2009/106419 discloses macrolide compounds having a five-membered lactone ring fused to the erythromycin scaffold and being substituted with specific side chains, which macrolide compounds, without having significant antibacterial activity, inhibit phosphodiesterases and in particular selectively inhibit PDE4. These macrolides are useful for the treatment and/or prevention of inflammatory and allergic diseases as well as proliferative diseases such as e.g. cancer. Preferred macrolide compounds according to WO2009/106419 have the following formula:

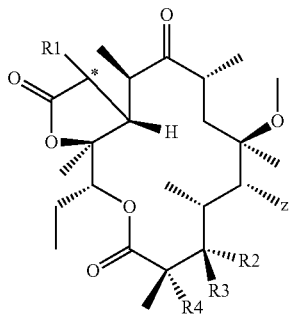

wherein e.g.
R1 is a residue —Y—X-Q;
Y is S, SO or SO$_2$;
X is a bond or a linear group consisting of hydrogen atoms and 1 to 9 atoms selected from C, N, O and S, of which up to 2 atoms can be N and one atom can be O or S, one carbon atom can appear as a CO group and the sulphur atom can appear as an SO$_2$ group and two adjacent C atoms can be present as —CH═CH— or —C≡C— and which group X is unsubstituted or is substituted with —COO—W or —CONH—W;
Q is a residue —V-A1-L-A2-W or —NR10R11, if X does not represent a bond;
V is an optionally substituted divalent aromatic or heterocyclic group;
W is optionally substituted aryl or heterocyclyl;
A1 and A2 are, independently of each other, either absent or a C$_1$-C$_4$alkylene group;
L is a —O—, —S—, —SO$_2$—, —NH—, —CO—, —(CO)O—, —O(OC)—, —(CO)NH—, —NH(CO)—, —(SO$_2$)NH—, —HN(SO$_2$)—, —HN(CO)NH—, —O(CO)NH—, —NH(CO)O—, or can also be absent if A1 and/or A2 are present;
R2 is OR2a or

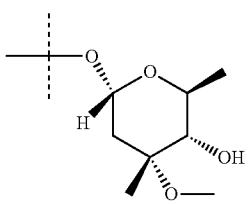

wherein

represents the linking bond;
R2a is hydrogen, acetyl, —(C═O)CH$_2$NR2bR2c, or —(C═O)CH$_2$CH$_2$NR2bR2c;
R2b and R2c independently of each other, are hydrogen or C1-C6 alkyl which can be substituted or unsubstituted and wherein up to two atoms can be N, O or S and one carbon atom can appear as C═O or, taken together with the nitrogen atom to which they are linked, form a 4-7 membered-ring of which up to two atoms can be N, O or S and one carbon can appear as C═O;
R3 is hydrogen or
R2 and R3 taken together with the carbon atom to which they are linked, represent a C═O group;
R4 is hydrogen or
R2 and R4 taken together with the bond between the carbon atoms to which they are linked, represent a double bond between said carbon atoms;
Z is

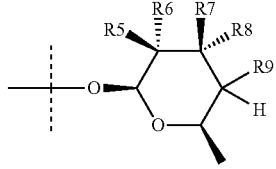

wherein

represents the linking bond;
R5 is hydrogen or —OR5a or —NR5bR5c;
R6 is hydrogen or —OR6a or —NR6bR6c; or
R5 and R6 taken together with the carbon atom to which they are linked, represent a C═O group;
R7 is hydrogen or —OR7a or —NR7bR7c;
R8 is hydrogen or —OR8a or —NR8bR8c; or
R7 and R8 taken together with the carbon atom to which they are linked, represent a C═O group; or one of
R5 and R6 taken together with one of
R7 and R8 represent a group of formula —NR56(CO)O— or —O(CO)NR78-
R9 is hydrogen or
R8 and R9 taken together with the bond between the carbon atoms to which they are linked, represent a double bond between said carbon atoms;
R5a, R6a,
R7a and R8a, independently of each other, are hydrogen or C1-C6 alkyl which can be substituted or unsubstituted and wherein one or more single bonds can be replaced by double and/or triple bonds and where one carbon atom can appear as C═O and up to two atoms can be N, O or S;
R56 and R78 are hydrogen or C1-C6 alkyl;
R5b, R5c,
R6b, R6c,
R7b, R7c,
R8b and R8c independently of one another, are hydrogen, C1-C6alkyl which can be substituted or unsubstituted and up to two atoms can be N, O or S and where one carbon atom can appear as C═O, or —(C═O)heterocyclyl or, taken together with the nitrogen atom to which they are linked, form a 4-7 membered-ring of which up to two atoms can be N, O or S and one carbon can appear as C═O;
R10 and R11 are independently selected from hydrogen, methyl; from optionally substituted groups selected from aryl; aralkyl; heterocyclyl and heterocyclylalkyl groups, and one of R10 and R11 can also be a group -L-A2-W; and

* indicates a chiral centre which is in the (R) or (S) form;
wherein
Z is a moiety other than the group of formula

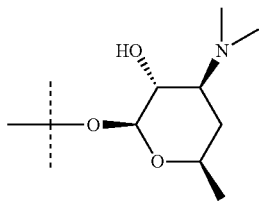

present in conventional macrolide compounds, which exhibit a substantial antibacterial activity, or a hydroxyl-protected variant of said moiety.

WO2011/018510 discloses macrolide compounds having a 11,12-cyclic carbamate substructure having the formula

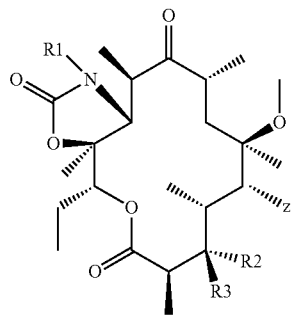

wherein R1 is a residue —X-Q and X, Q and Z and the other residues have the same or a similar meaning as in WO2009/106419. These compounds are also active as inhibitors of phosphodiesterase, in particular PDE4, without having significant antibacterial activity.

The macrolide compounds disclosed WO2009/106419 and WO2011/018510 show many favorable application-technical properties but still leave room for further improvement.

For example, the compound of Example 9 of WO2009/106419, which has the following formula:

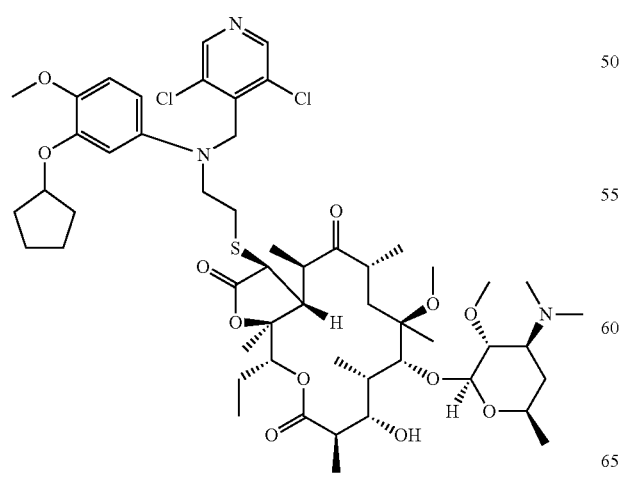

shows good to moderate PDE4-inhibiting activity, is antibacterially inactive against many pathogenic types of bacteria, shows moderate bioavailability, but inhibits, on the other hand, the activity of the hERG channel rather strong.

The compound of Example 10 of WO2009/106419, which has the following formula:

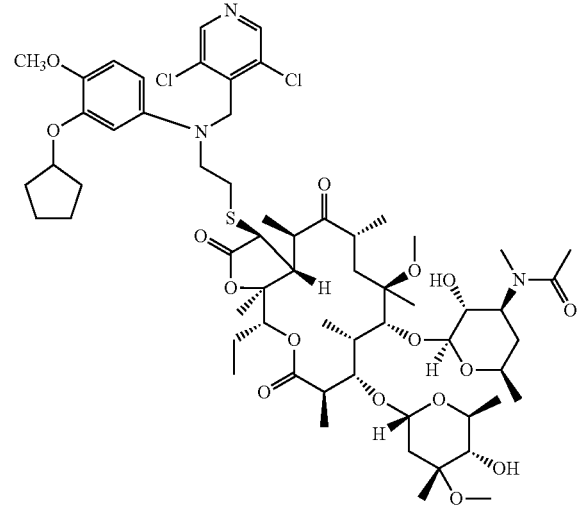

shows excellent PDE4-inhibiting activity and particularly good oral bioavailability, exhibits, on the other hand however, still a strong remaining antibacterial activity against certain types of bacteria.

The compound of Example 15 WO2009/106419, which has the following formula:

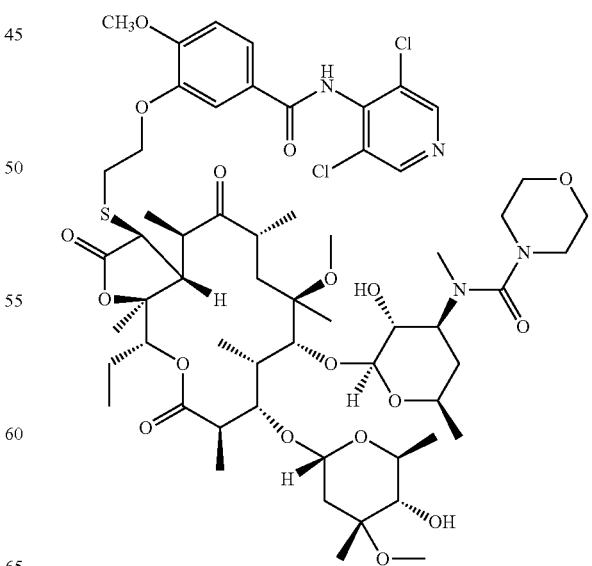

on the other hand, shows excellent PDE4-inhibiting activity, this time combined with strongly reduced antibacterial activity against a broad spectrum of different kinds of bacteria. Its oral bioavailability, however, is rather low.

Similarly, the compound of Example 2 of WO2001/018510 which has the formula:

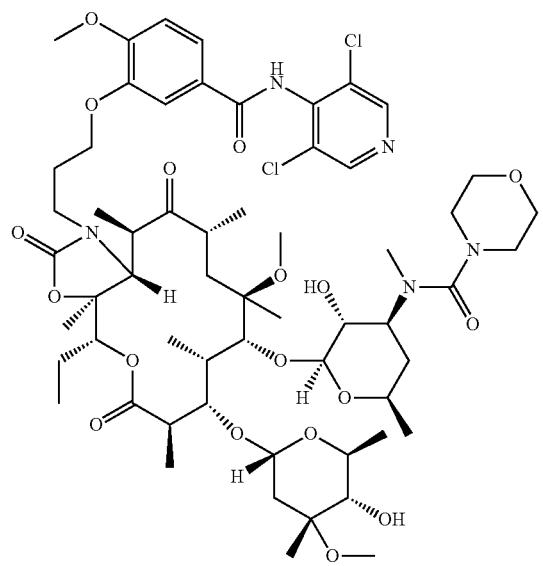 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)N3CCOCC3)[C@H]2O)[C@](C)(OC)C[C@@H](C)C(=O)[C@H](C)[C@H]2N(CCCOc3cc(C(=O)Nc4c(Cl)cncc4Cl)ccc3OC)C(=O)O[C@]12C]

shows a moderate to good oral bioavailability and an acceptable hERG channel inhibiting activity. Its PDE4-inhibiting activity, on the other hand, could still be better and, although its antibacterial activity is low against many bacterial strains, there are some strains like e.g. certain strains of *Propionibacterium acnes*, against which said compound is still very active and wherein it could thus induce resistance against macrolides.

It has now been found, that the new macrolide compound of formula (I) given below provides an excellent pharmaceutical overall profile. In particular, it shows excellent PDE4-inhibiting activity combined with strongly reduced antibacterial activity against a very broad spectrum of different types of bacteria and particularly good oral bioavailability. Furthermore, it does not inhibit the hERG channel activity.

Subject of the present invention is accordingly a macrolide compound of the formula (I):

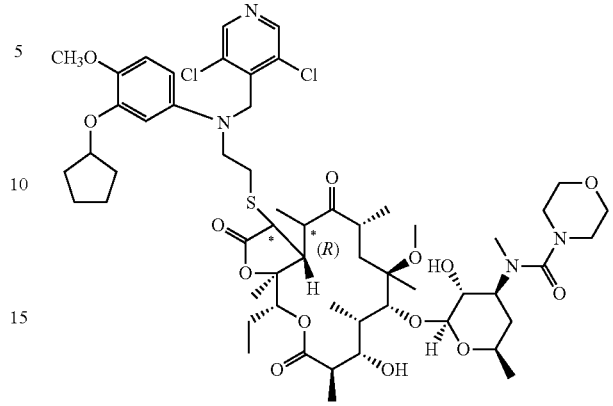

wherein

\* indicates a stereocentre which is in (R) or (S) configuration, or a pharmaceutically acceptable salt or ester thereof.

A more specific subject of the present invention is the macrolide of formula (I-A):

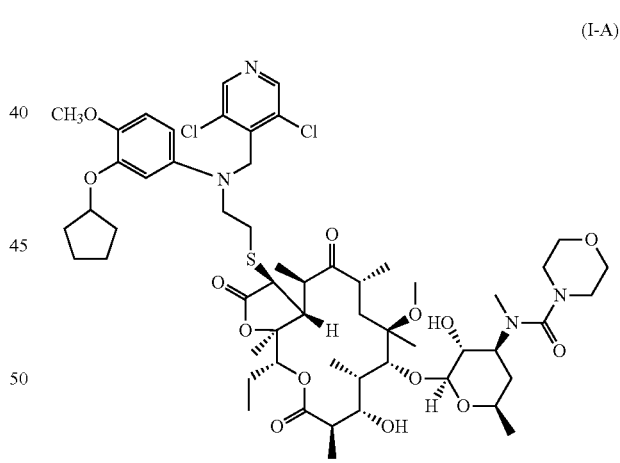

or a pharmaceutically acceptable salt or ester thereof.

Table 1 provides a comparison of the mentioned drug properties as compared to the mentioned closely related prior art macrolides compound and other macrolide derivatives of similar structure:

TABLE 1
| Compound | IC50 PDE4 (μM) (U937) | MIC (μg/ml) S. aureus ATCC-29213 | MIC (μg/ml) S. pyogenes ATCC-19615 | MIC (μg/ml) M. catarrhalis QK34 | MIC (μg/ml) H. influenzae 3168 |
|---|---|---|---|---|---|
| 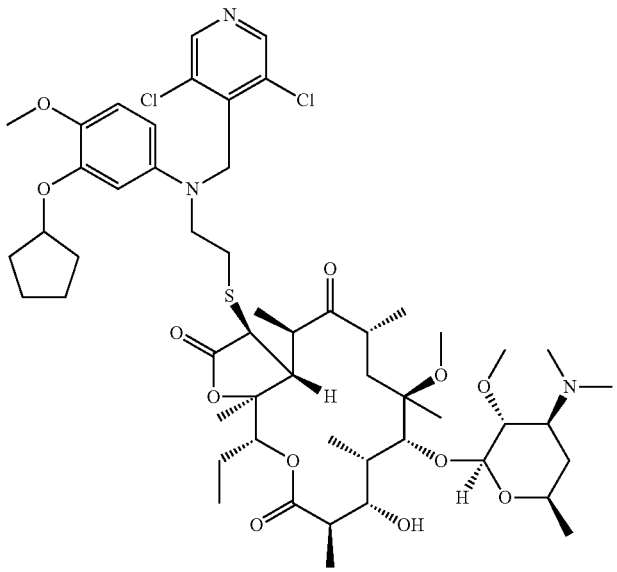WO2009/106419, Expl. 9 | 0.30 | 8 | 32 | >32 | >32 |
| 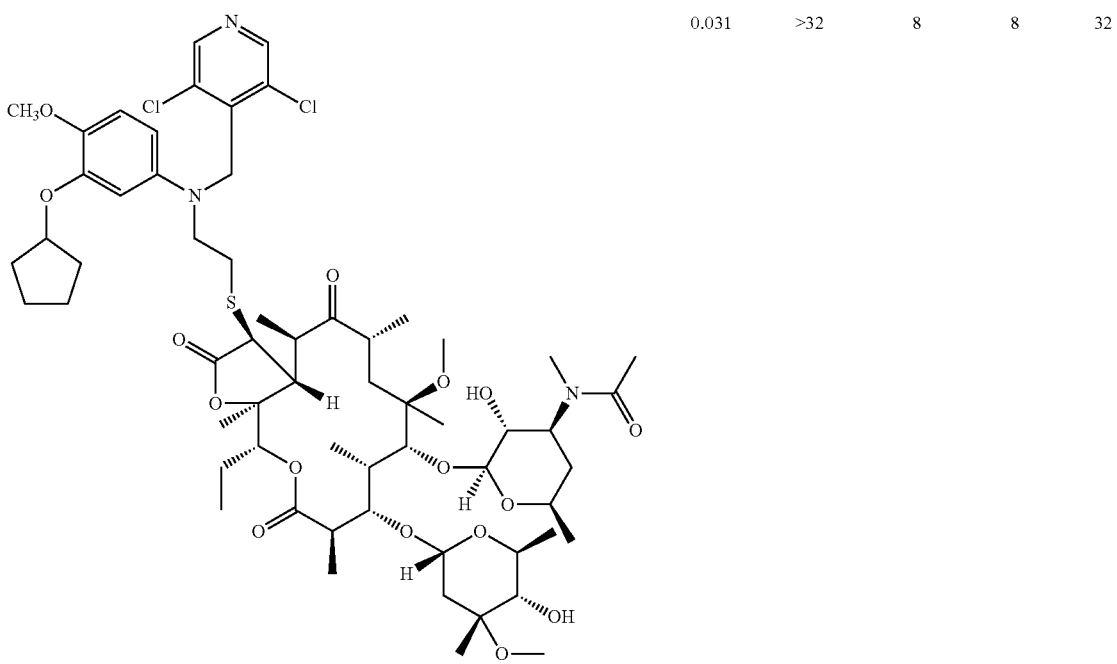WO2009/106419, Expl. 10 | 0.031 | >32 | 8 | 8 | 32 |

TABLE 1-continued
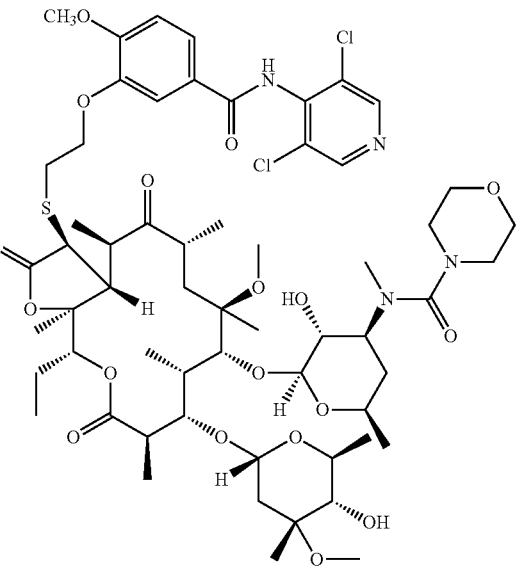
WO2009/106419, Expl 15
0.071 >32 >32 >32 >32
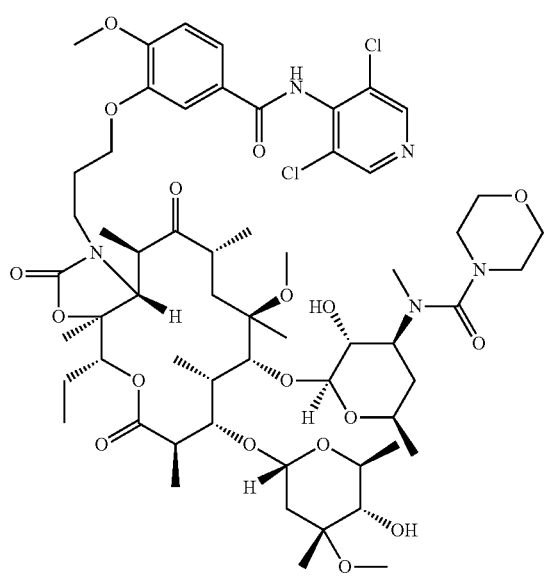
WO2011/018510, Expl. 2
0.876 >32 >32 >32 >32

TABLE 1-continued
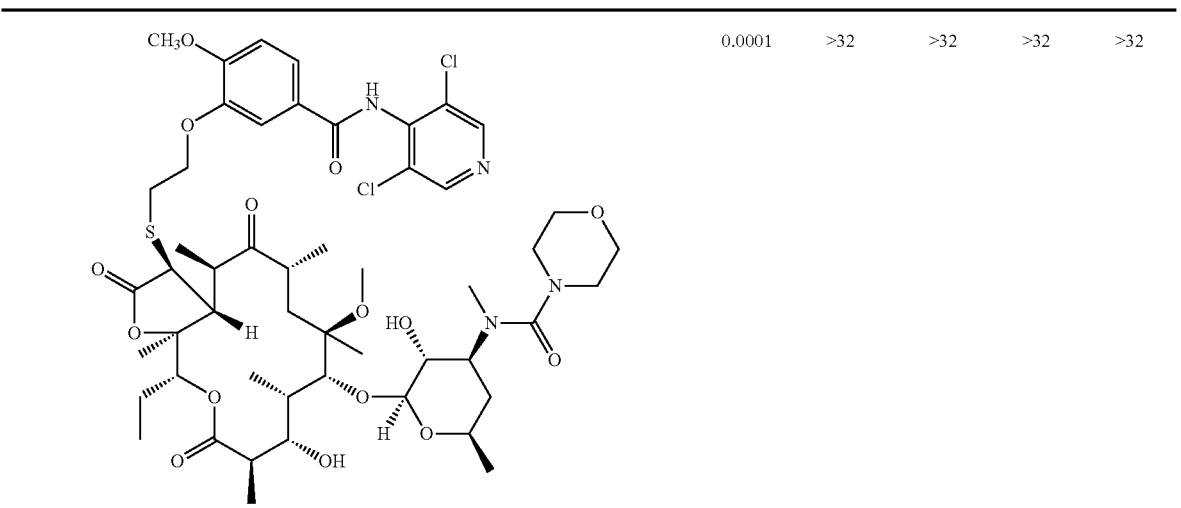
Comparative Compound A
0.0001   >32   >32   >32   >32
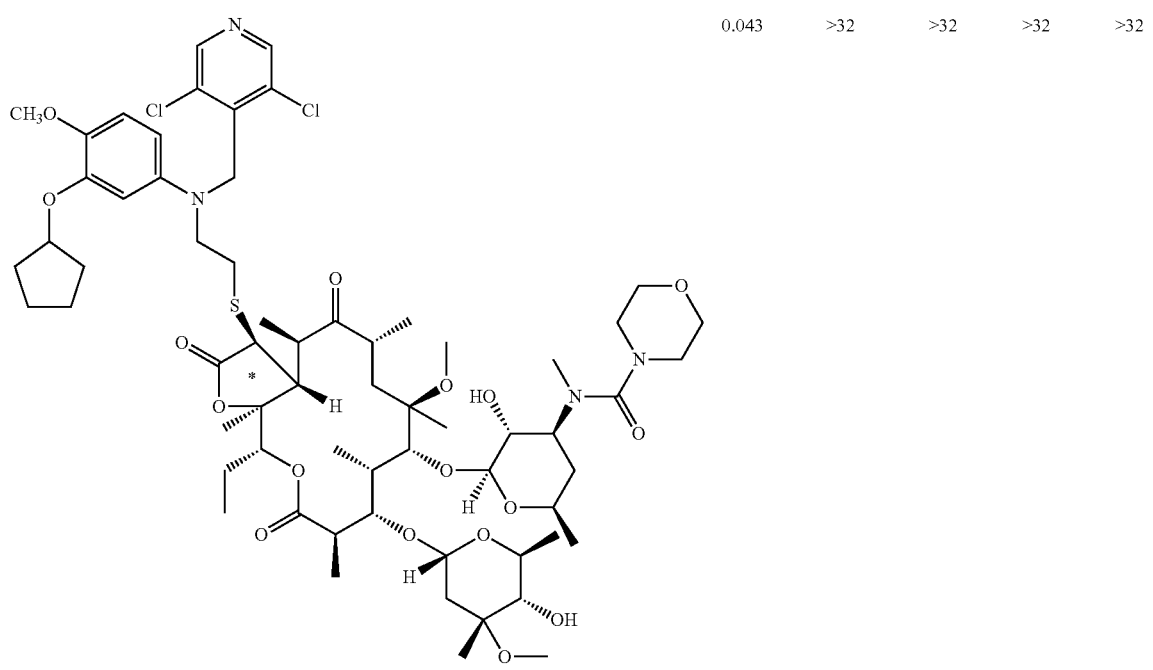
Comparative Compound B
0.043   >32   >32   >32   >32

TABLE 1-continued
| | | | | | |
|---|---|---|---|---|---|
| 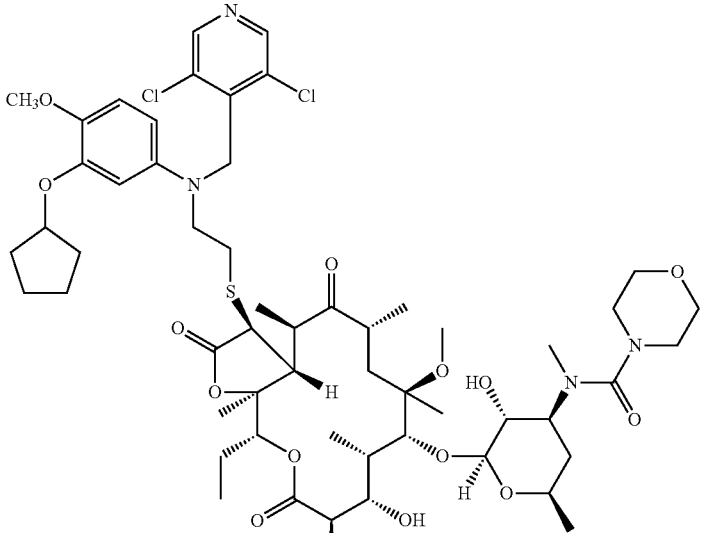 Compound of Formula (I-A) according to the present invention | 0.035 | >32 | >32 | >32 | >32 |
| Compound | MIC (g/ml) P. acnes EG7NS | MIC (g/ml) P. granulosum EG13NS | Oral bioavail. (mouse F %) | Blocking of hERG @ 1 µM (% remaining tail current) | Blocking of hERG @ 10 µM (% remaining tail current) |
|---|---|---|---|---|---|
| 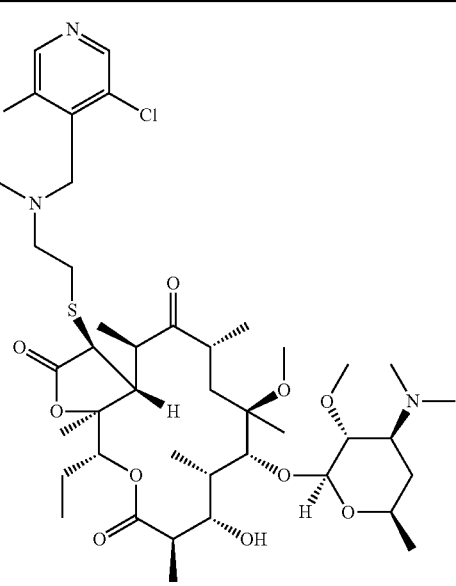 WO2009/106419, Expl. 9 | 4 | 4 | 9 | 23.7 | 3.7 |

TABLE 1-continued
| | | | | |
|---|---|---|---|---|
| 4 | 2 | 25.5 | 95.9 | 85.5 |
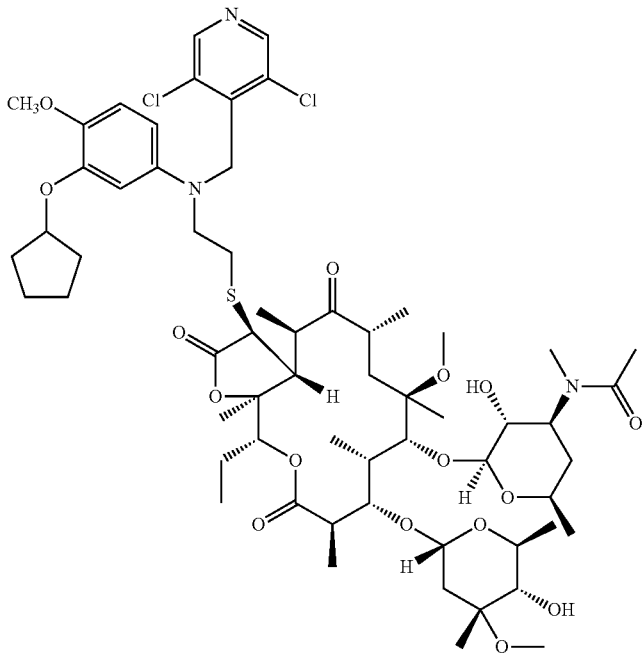
WO2009/106419,
Expl. 10
| | | | | |
|---|---|---|---|---|
| >32 | >32 | 4.6 | 100 | 98.6 |
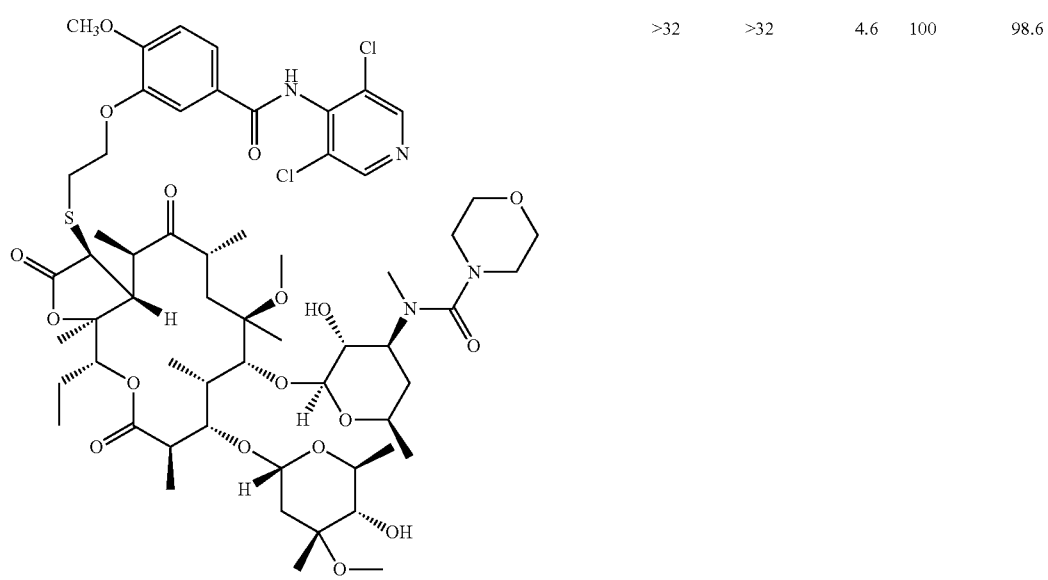
WO2009/106419,
Expl 15

TABLE 1-continued
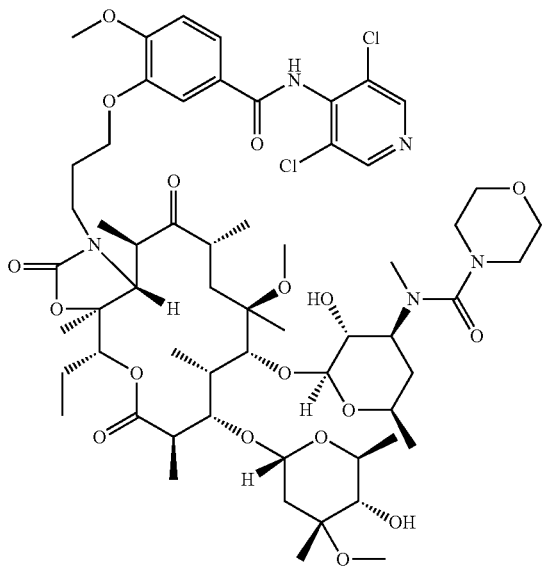 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)N3CCOCC3)[C@H]2O)[C@](C)(OC)C[C@@H](C)C(=O)[C@H](C)[C@H]2N(CCCOc3cc(C(=O)Nc4c(Cl)cncc4Cl)ccc3OC)C(=O)O[C@]12C]
WO2011/018510,
Expl. 2
2    >32    16.2    99    84
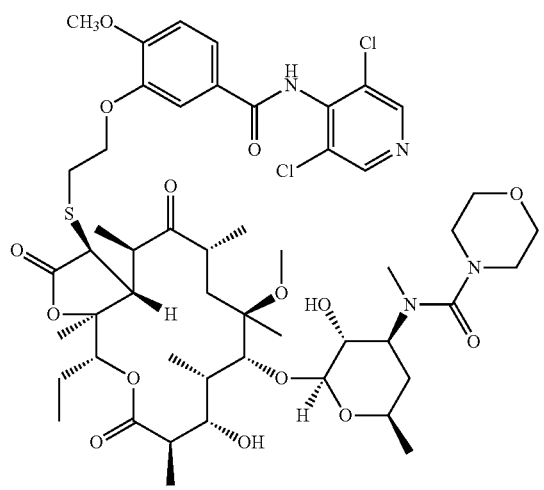
Comparative Compound A
>32    >32    11.5    99.9    100

TABLE 1-continued

| | | | | | |
|---|---|---|---|---|---|
| | >32 | >32 | 1.5 | 99.2 | 82.9 |

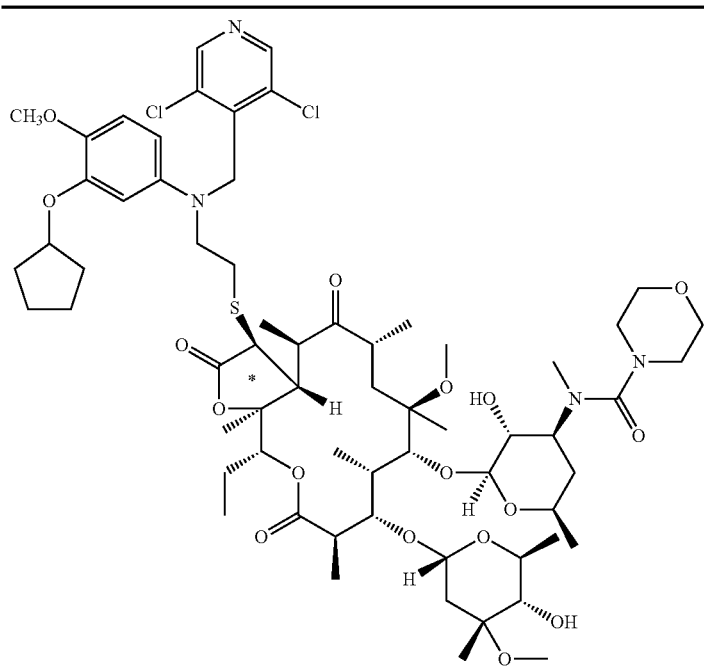

Comparative Compound B

| | | | | | |
|---|---|---|---|---|---|
| | >32 | >32 | 22.8 | 99.9 | 98 |

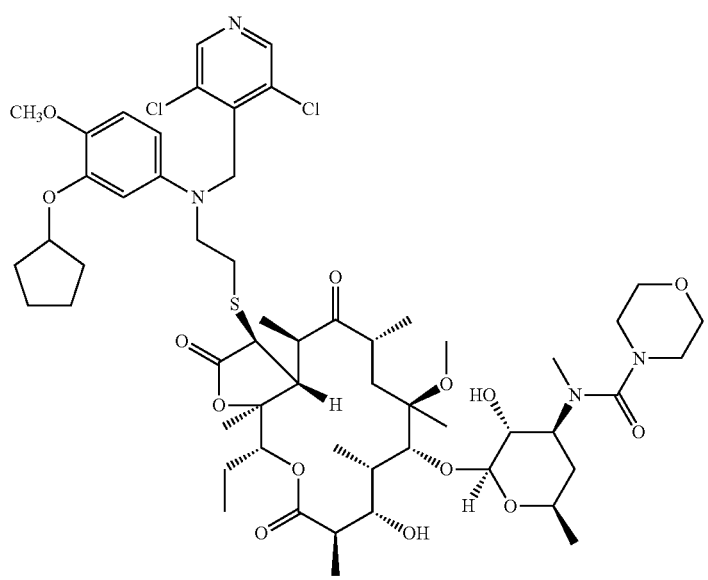

Compound of Formula (I-A) according to the present invention

For the purposes of the present invention the term "macrolide compound" is understood to include the separate stereomeric forms of the compounds as well as diastereomeric mixtures.

The macrolide compound according to the invention can, if desired, be present and used as a pharmaceutically acceptable acid addition salt. Not only salts with inorganic acids, but also salts with organic acids come into consideration. Hydrochlorides, hydrobromides, sulfates including hydrogensulfates, nitrates, citrates, acetates, trifluoroacetates, maleates, succinates, methanesulphonates, p-toluenesulphonates and the like are examples of such salts.

Pharmaceutically acceptable esters as understood herein are in particular in vivo cleavable esters like, in particular, esters with of the 2'-hydroxy group of the sugar moiety. Suitable esters are e.g. acetates, pivaloyl esters, tartrates, maleates, succinates, and the like.

Particularly preferred is the compound of formula (I) as such, i.e. not in form of a salt or ester.

The compound of the invention exhibits excellent inhibitory activity towards phosphodiesterases (PDEs), in particular towards PDE4, in particular human phosphodiesterases (PDEs) and human PDE4, which has been shown to be involved in particular in inflammatory processes (cf. e.g. Lipworth B. J., Lancet (2005) 365, p. 167 or Giembycz M. A., Curr. Opin. Pharmacol. (2005), 5, p. 238). The use of the compound according to the present invention for the treatment of diseases and disorders in a subject, selected from animals like mammals, and, particularly, humans, which can be ameliorated or relieved by inhibition of phospodiesterases, in particular phosphodiesterase 4 (PDE4), is therefore a further aspect of the present invention. Based on this activity the compound of the present invention is particularly useful for the prevention and/or treatment of inflammatory diseases as well as for the treatment and/or prevention of allergic and autoimmune diseases and for the prevention and/or treatment of diseases associated with uncontrolled growth, proliferation and/or survival of cells of such subjects, e.g. cancer. The use for humans is preferred.

Particularly important examples of diseases, for which the compound of the present invention or its pharmaceutically acceptable acid addition salts or esters can be used, are chronic obstructive pulmonary disease (COPD), asthma, rheumatoid arthritis, psoriasis, atopic dermatitis, inflammatory bowel disease and the treatment of human or animal diseases associated with uncontrolled growth, proliferation and/or survival of cells of such subjects, i.e. cancer diseases.

The compound of the present invention and its pharmaceutically acceptable acid addition salts or esters can however also be used for the prevention and/or treatment of diseases such as chronic bronchitis, emphysema, urticaria, allergic rhinitis, allergic conjunctivitis, septic shock, adult respiratory distress syndrome and multiple sclerosis.

Most preferred is the use of the compound of the present invention or its pharmaceutically acceptable acid addition salts or esters for the treatment of chronic obstructive pulmonary disease (COPD) or psoriasis.

A further embodiment of the present invention are therefore medicaments comprising the Compound of Formula (I) or a pharmaceutically acceptable acid addition salt or ester thereof for the prevention and, preferably, for the treatment of inflammatory diseases, allergic or autoimmune diseases or diseases associated with uncontrolled growth, proliferation and/or survival of cells of subjects selected from animals, e.g. mammals, and preferably humans, in particular in the form of pharmaceutical preparations for enteral (oral) administration. The products in accordance with the invention can be administered, in particular perorally such as in the form of tablets, film coated tablets, sugar coated tablets, hard and soft capsules, solutions, emulsions or suspensions, but also rectally, such as in the form of suppositories, or parenterally e.g. by injection, or nasally, or by inhalation or transdermally, or locally for example by topical administration. Particularly preferred, the compounds are administered topically or, more preferably, orally.

Pharmaceutical compositions containing the compound according to the invention or pharmaceutically acceptable salts or esters thereof can be prepared using conventional procedures familiar to those skilled in the art, such as by combining the ingredients into a dosage form together with suitable, non-toxic, inert, therapeutically compatible solid or liquid carrier materials and, if desired, one or more of usual pharmaceutical adjuvants.

It is contemplated that the compound of the present invention is embodied e.g. into compositions of suitable oral dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as microcrystalline cellulose, calcium phosphate or lactose; disintegrating agents, such as starch, crosslinked carboxymethylcellulose sodium or crosslinked polyvinylpyrrolidone; and lubricating agents, such as talc, magnesium stearate, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, film coated tablets, sugar coated tablets and hard capsules there can be used, for example, lactose, maize starch or derivatives thereof, talc, stearic acid or its salts. Suitable carriers for soft capsules are, for example, vegetable oils, waxes, fats and semi-solid and liquid polyols (depending on the nature of the active substance). Suitable carrier materials for the preparation of solutions and syrups are, for example, water, alcohols, polyols, saccharose, invert sugar and glucose.

As pharmaceutical adjuvants there are contemplated the usual preservatives, solubilizers, stabilizers, wetting agents, emulsifiers, sweeteners, colorants, flavoring agents, salts for adjusting the osmotic pressure, buffers, coating agents and antioxidants.

For the treatment and/or prevention of inflammatory and allergic diseases in mammals, humans and non-humans, a daily dosage of about 10 mg to about 2000 mg, especially about 50 mg to about 1000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 10 mg, 50 mg, 100 mg, 250 mg, 500 mg and 1000 mg can be contemplated.

The preparation of compound of formula I can e.g. be carried according or analogous to methods described in WO2009/106419, the full disclosure of which is considered to be part of the present description.

A preferred way for preparing the compound of formula (I) of the present application is shown in the following reaction scheme, wherein the asterix * indicates a stereocentre of the compounds which is in (R) or (S) configuration, starting from Clarithromycin:

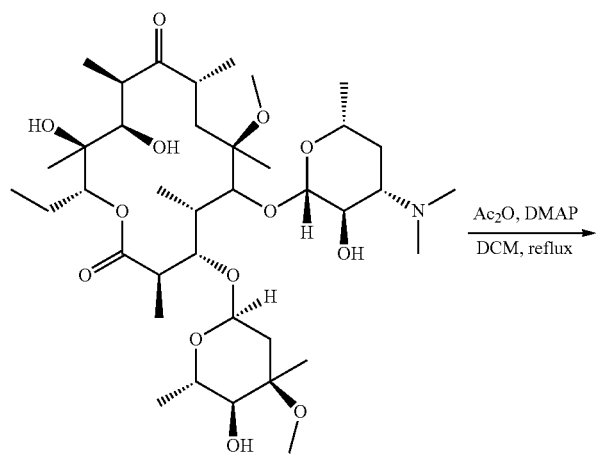
Clarithromycin
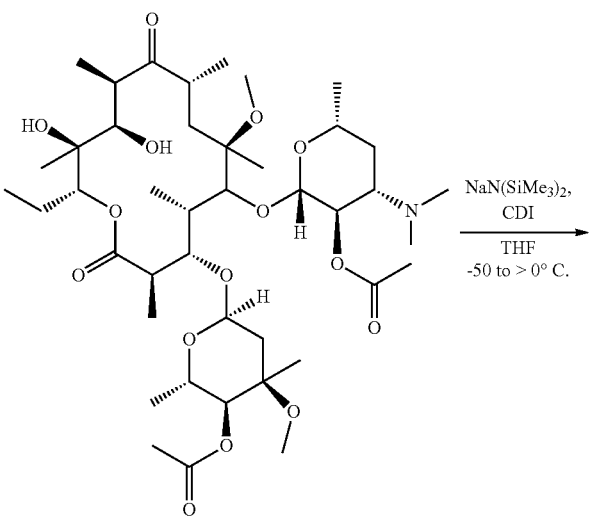
Comp. 1
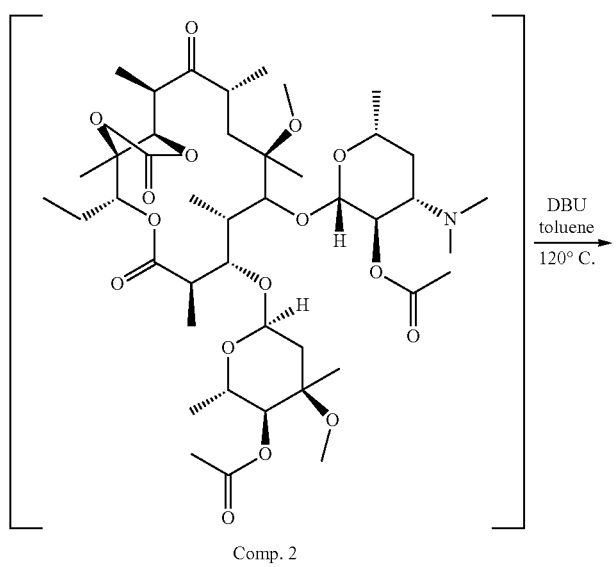
Comp. 2
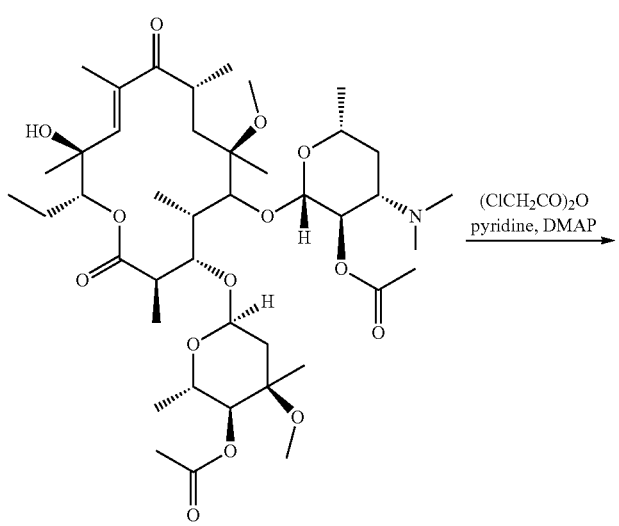
Comp. 3

-continued
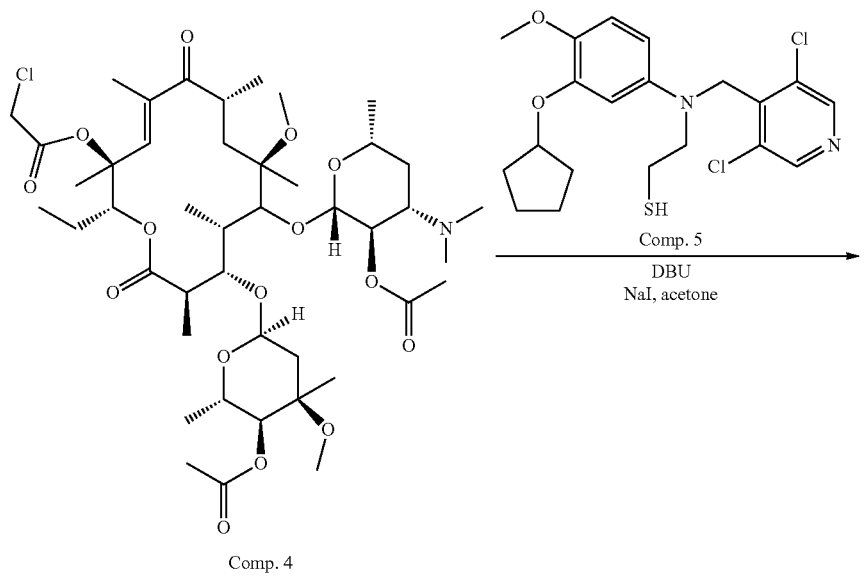
Comp. 4
Comp. 5
DBU
NaI, acetone
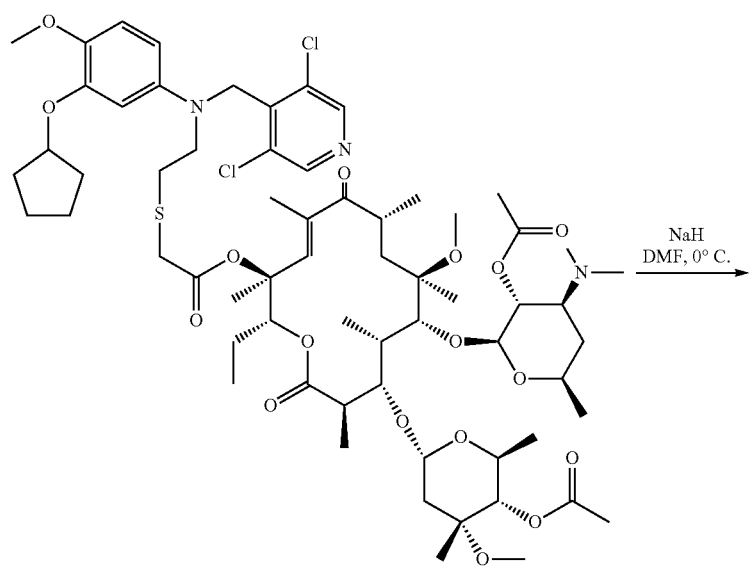
Comp. 6
NaH
DMF, 0° C.

-continued
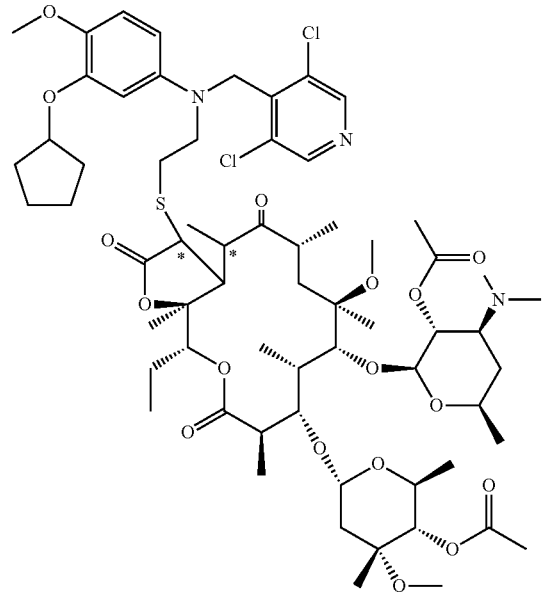
Comp. 7
HCl
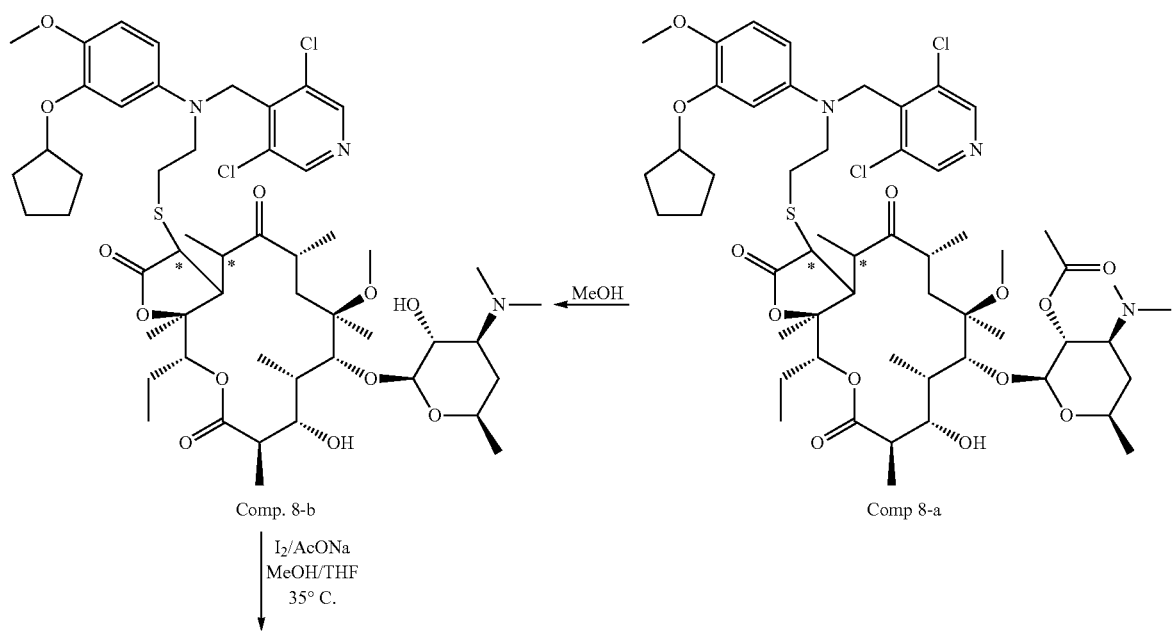

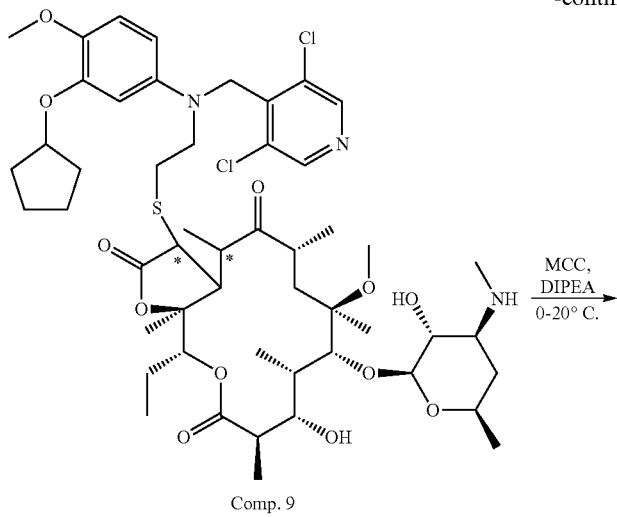

Comp. 9

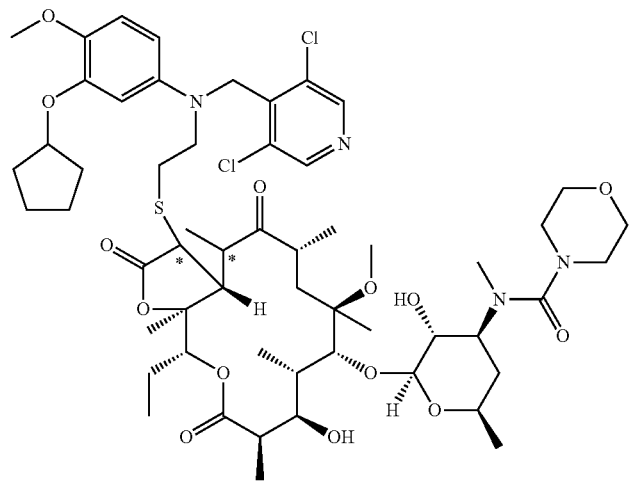

Compound of Formula (I)

Clarithromycin is converted to Compound 1 by refluxing it in dichloromethane (DCM) with acetic acid anhydride and 4-dimethylaminopyridine (DMAP).

Compound 1 is then dissolved in THF at −50° C. and treated with a solution of sodium bis(trimethylsilyl)amide in THF. Then carbonyldiimidazole (CDI) in THF is added. The reaction mixture is kept at about −50° C. for 15 min to 1 hour and then warmed to 0° C. and kept at 0-5° C. for some hours (1 to 6) and the obtained Compound 2 is optionally isolated and optionally purified.

Compound 2 in THF is heated to 80 to 130° C. for several hours (5 to 30) in the presence of 1,8-Diazabicyclo[5.4.0]undec-7-ene (DBU) and the obtained Compound 3 is isolated and optionally purified.

The hydroxy group at position 12 of Compound 3 is esterified according to standard methods by treatment for example with 2-chloro acetic acid, an activating agent like DCC and DMAP or with 2-chloro acetic anhydride, pyridine, DMAP in a solvent such as methylene chloride to obtain Compound 4.

Compound 4 is then treated with Compound 5, which is e.g. prepared as described hereinafter, in acetone in the presence of a base such as DBU and sodium iodide to give Compound 6.

Compound 6 is then treated at a temperature between about −20° C. and 5° C. with an alkali metal base such as NaH or potassium tert.-butoxide or LDA in an aprotic solvent such as DMF or THF to give Compound 7.

The protected cladinose sugar moiety of Compound 7 is cleaved by treating Compound 7 with an acid such as hydrochloric acid in a solvent such as acetonitrile to give Compound 8-a, which is deprotected according to methods well known in the art, e.g. with methanol at temperature between 20° C. and 40° C., to give Compound 8-b.

The 3'-dimethylamino group of Compound 8-b is then monodemethylated by reaction with halogen, preferably iodine, in an inert solvent such as methanol, dioxane, aqueous dioxane, THF, aqueous THF or DMF or a mixture thereof in the presence of a base such as alkali hydroxide or in particular sodium acetate, sodium propionate or sodium benzoate at a temperature of about −10° C. to 50° C. during 5 to 72 hours to yield Compound 9. The conversion is described e.g. in U.S. Pat. No. 3,725,385. Preferably, the conversion is done with iodine in a mixture of methanol and THF in the presence of sodium acetate as base at a temperature of about 30 to 40° C.

Compound 9 is finally reacted with 4-morpholinecarbonyl chloride (MCC) in the presence of a base like NaH or, preferably, diisopropylethylamine (DIPEA) in an inert solvent like THF or DMF at a temperature of about 0° C. to 25° C. to yield the desired end product the Compound of Formula (I), which can then, if desired, be further converted to a pharmaceutically acceptable acid addition salt or ester according to methods well known in the art.

Compound 5, required for the conversion of Compound 4 to Compound 6, can be prepared e.g. according to the following reaction scheme:

Compound 5-B is reacted with about two equivalents of potassium thioacetate in the presence of sodium iodide in an inert solvent like e.g. DMF at a temperature of about 50 to 60° C. to yield Compound 5-C, which is finally saponified with ammonia/methanol at a temperature of about 0° C. to 20° C. to yield Compound 5.

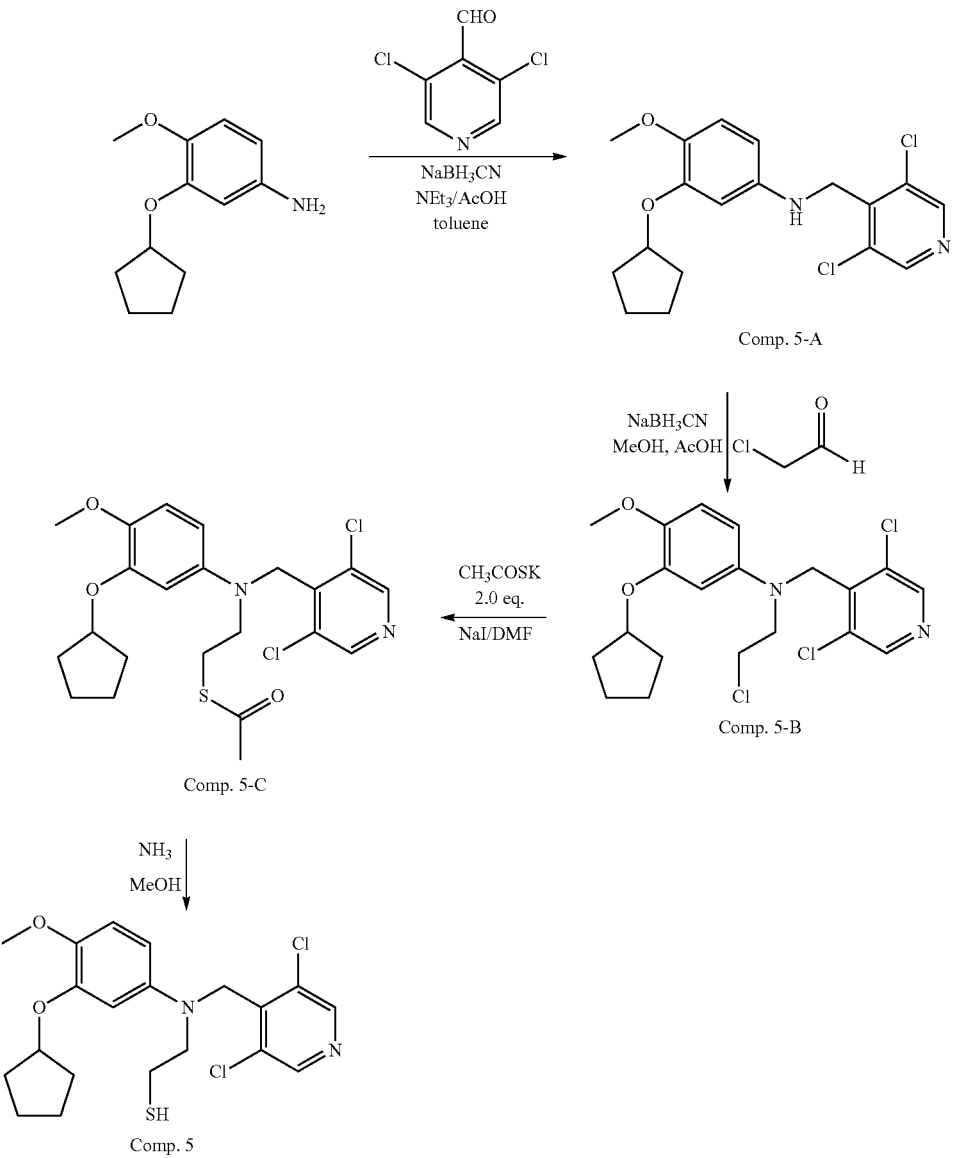

To a mixture of 3-cyclopentyloxy-4-methoxy-phenylamine (obtained for instance according to Garcia et al., JOC, 2005, 70, p 1050) and 3,5-dichloro-4-pyridinecarboxaldehyde in an inert solvent like THF are added triethylamine and acetic acid acetic acid and then sodium cyanoborohydride (NaBH$_3$CN). The mixture is stirred at about room temperature for about 30 min to about 2 hours. to yield Compound 5-A by direct. reductive amination.

Compound 5-A dissolved methanol is then reacted at about room temperature with a mixture of chloroacetaldehyde and water in the presence of NaBH$_3$CN and acetic acid for about 3 to 10 hours to yield Compound 5-B

EXAMPLE

Abbreviations: DBU for diazabicycloundecane; DCM for dichloromethane; DIPEA for diisopropylethylamine (Huenig's base); DMF for dimethylformamide; MeOH for methanol; THF for tetrahydrofuran; MS for mass spectrometry; NMR for nuclear magnetic resonance.

The numbers of the compounds referred to in the Example correspond to the numbers of the compounds mentioned in the reaction schemes above.

Synthesis of Compound 6

1.8 g (2.02 mmol) of Compound 4, prepared according to WO2006084410, Example 1, A] to D], and 0.9 g (2.02 mmol) of Compound 5, prepared as described below, are dissolved in 20 ml DMF, then 0.92 g (6.06 mmol) of DBU and 121 mg (0.81 mmol) of NaI are added. The solution is stirred for 1.0 hour at room temperature. The solvent is removed in vacuo, the residue is poured into 50 ml of 0.5M aq. $KH_2PO_4$ solution and the resulting mixture is extracted twice with 50 ml of DCM. The combined organic layers are washed with water and brine, dried over anhydrous $Na_2SO_4$ and concentrated in vacuo to give the crude product, which is purified by silica gel column chromatography (eluent: DCM/MeOH=100/1 to 50/1) to give 1.7 g of the desired product as light yellow foam.

MS(ESI): 640.9 $[M+2H]^{2+}$

1H-NMR (CDCl3): (diagnostic signals only) 8.44 (s, 2H); 6.74 (d, 1H); 6.59 (s, 1H); 6.50 (s, 1H); 6.48 (dd, 1H); 5.68 (d, 1H); 4.97 (bs, 1H); 4.66-4.72 (m, 3H); 4.60 (m, 1H); 4.48 (s, 2H); 4.35 (bs, 1H); 3.78 (bs, 4H); 3.63 (bs, 1H); 3.56 (dd, 1H); 3.20-3.33 (m, 6H); 3.16 (s, 3H); 2.66-2.76 (m, 3H); 2.40 (d, 1H); 2.26 (bs, 6H); 2.14 (s, 3H); 2.04 (s, 3H); 0.92-0.99 (m, 3H); 0.85 (t, 3H).

Synthesis of Compound 7

2.0 g (1.56 mmol) of Compound 6 are dissolved under nitrogen atmosphere in 30 ml DMF, the solution is cooled to −20° C., 54 mg (1.4 mmol, 60% dispersion in oil) of NaH is added and the mixture is stirred at −20° C. until HPLC indicated no starting material remained. Then 100 ml water is added, the mixture is extracted 3 times with 50 ml DCM and the combined organic layers are washed with water and brine, dried over anhydrous $Na_2SO_4$ and concentrated in vacuo to give 2.6 g of the crude product as brown oil, which is purified by silica gel column chromatography eluting with DCM/MeOH (V/V, 60/1) to afford 1.1 g of the desired product as yellow foam.

MS(ESI): 1282.5 $[MH]^+$ and 641.7 $[M+2H]^{2+}$

1H-NMR (CDCl3): (diagnostic signals only) 8.40 (s, 2H); 6.70 (d, 1H); 6.46 (s, 1H); 6.42 (dd, 1H); 5.38 (d, 1H); 4.93 (bs, 1H).

Synthesis of Compound 8-a 600 mg (0.47 mmol) of Compound 7 is dissolved in 15 ml acetonitrile, then 24 ml 1N hydrochloride acid is added. The reaction mixture is stirred at 30° C. for 16 h. The aqueous phase is adjusted to PH=7 with 2N aq. $NaHCO_3$ solution. The resulting mixture is extracted twice with 30 ml DCM, the combined organic layers are washed with water and brine, dried over anhydrous $Na_2SO_4$ and concentrated in vacuo to give 0.5 g of the crude product as yellow foam.

MS(ESI): 1080.4 $[MH]^+$ and 540.9 $[M+2H]^{2+}$

Synthesis of Compound 8-b 1.5 g (1.39 mml) of compound 4 is dissolved in 30 ml of MeOH and the solution is stirred for 16 h at 30° C. Then the solvent is removed in vacuo and the residue is purified by flash chromatography on silica gel (DCM/MeOH 60:1) to afford 400 mg of the desired product.

MS(ESI): 1038.4 $[MH]^+$ and 519.9 $[M+2H]^{2+}$

1H-NMR (CDCl3): (diagnostic signals only) 8.43 (s, 2H); 6.75 (d, 1H); 6.50 (s, 1H); 6.44 (dd, 1H); 5.52 (d, 1H); 4.71 (bs, 1H); 4.58-4.61 (m, 3H); 4.40 (s, 1H); 3.77 (s, 3H); 3.71 (s, 1H); 3.47-3.60 (m, 5H); 3.37-3.42 (m, 1H); 2.83-2.88 (m, 1H); 2.47-2.49 (m, 1H); 2.06-2.08 (m, 1H); 1.44 (s, 3H); 1.25-1.38 (m, 9H); 1.08-1.14 (m, 9H); 0.83 (t, 3H).

Synthesis of Compound 9

200 mg (0.15 mmol) of compound 5 is dissolved in a mixture of MeOH and THF (10 ml MeOH/2 ml THF) and 63 mg (0.77 mmol) sodium acetate is added. The mixture is stirred at 30-35° C. or 30 minutes, then 177 mg $I_2$ (0.70 mmol) is added. The black reaction mixture is stirred at 30-35° C. for 5 h. Saturated aq. $Na_2S_2O_3$ solution is added until the color of $I_2$ faded. The solvent is removed in vacuo, the residue is poured into 30 ml water and is extracted twice with 50 ml DCM. The combined organic layers are washed with water and brine, dried over anhydrous $Na_2SO_4$ and concentrated in vacuo to give the crude product, which is purified by flash chromatography on silica gel (DCM/MeOH 100:1-20:1) to afford 70 mg of the desired product as yellow foam.

MS(ESI): 1026.4 $[MH]^+$ and 513.8 $[M+2H]^{2+}$

Synthesis of the Compound of Formula (I) According to the Invention

To a solution of 10.0 g (4.88 mmol) of Compound 9 in 150 ml THF is added 1.89 g (14.63 mmol) DIPEA at 0-5° C. under nitrogen atmosphere. The mixture is stirred for 30 minutes and 1.46 g (9.75 mmol) of 4-morpholinylcarbonyl chloride (MCC) is added. The mixture is stirred at 20° C. for 20 h. The solvent is removed under reduced pressure. The residue is dissolved in 200 ml DCM and washed with water and brine, dried over anhydrous $Na_2SO_4$ and concentrated in vacuo to give the crude product, which is purified by flash chromatography on silica gel (DCM/MeOH=200:1-50:1) to afford 4.6 g of the desired product as a yellow foam.

MS(ESI): 1137.5 $[M+H]^+$, 569.2 $[M+2H]^{2+}$

1H-NMR (DMSO-d6): 8.59 (s, 1H); 8.59 (s, 1H); 6.79 (d, 1H); 6.49 (d, 1H); 6.44 (dd, 1H); 5.33 (dd, 1H); 5.23 (d, 1H); 4.90 (d, 1H); 4.71 (m, 1H); 4.67 (d, 1H); 4.62 (d, 1H); 4.56 (d, 1H); 4.25 (s, 1H); 3.68 (s, 1H); 3.65 (m, 1H); 3.65 (s, 3H); 3.61 (m, 1H); 3.56 (m, 4H); 3.52 (m, 1H); 3.39 (m, 1H); 3.24 (dd, 1H); 3.20 (m, 1H); 3.12 (m, 2H); 3.08 (m, 1H); 3.05 (m, 2H); 2.93 (m, 1H); 2.88 (s, 3H); 2.78 (m, 1H); 2.71 (s, 3H); 2.59 (s, 1H); 2.56 (dd, 1H); 2.34 (m, 1H); 1.90 (m, 1H); 1.87 (m, 1H); 1.78 (m, 2H); 1.68 (1H); 1.67 (m, 2H); 1.66 (m, 2H); 1.63 (m, 1H); 1.55 (1H); 1.52 (m, 2H); 1.46 (m, 1H); 1.45 (m, 1H); 1.41 (s, 3H); 1.17 (s, 3H); 1.15 (d, 3H); 1.11 (d, 3H); 1.05 (d, 3H); 0.98 (d, 3H); 0.94 (d, 3H); 0.75 (t, 3H);

Synthesis of Compound 5-C

To a solution of 2.6 g (6.05 mmol) of compound 5-B, prepared according to WO2009098320, Example 15, A] and B], in 30 ml DMF is added 1.38 g (12.1 mmol) potassium thioacetate and 181 mg (1.21 mmol) sodium iodide. The reaction mixture is stirred at 60° C. for 5 h, then 100 ml water is added; the mixture is extracted twice with 100 ml ethyl acetate. The combined organic layers are washed with water and brine, dried over $Na_2SO_4$ and concentrated in vacuo to give 2.8 g of the desired product as yellow solid.

MS(ESI): 469.1 $[MH]^+$

Synthesis of Compound 5

8.0 g (17.0 mmol) of Compound 5-C is dissolved in 150 ml methanol, then ammonia gas is bubbled into the solution at 5° C. The resulting solution is stirred for 4 hours at this temperature under ammonia atmosphere, then evaporated under vacuum to give 7.5 g of the desired product as a yellow solid. The product is stored under an atmosphere of argon.

MS(ESI): 427.2 [MH]$^+$

The biological activity data of the Compound of Formula (I) according to the present invention and the comparative compounds given in Table 1 are determined as follows:

Enzyme Preparations:

PDE4 is partially purified from undifferentiated human monocytic cells (U937) according to Thorpy et al. 1992 (J. Pharmacol. Exp. Ther. 263: 1195). Cells are grown in Iscove's modified Dulbecco's medium (GIBCO) with 5% foetal bovine serum (GIBCO) and 100 μg/mL penicillin-streptomycin (GIBCO). Cells are broken by sonication and PDE4 is purified by anion-exchange chromatography on DEAE-Sepharose CL-6B (GE Healthcare). The final preparations are specific for cAMP and do not hydrolyze cGMP above the detection limit of the assay. In addition, PDE4 preparations are validated by inhibition studies with PDE4-specific and unspecific PDE inhibitors.

Enzyme Assays:

PDEs specifically hydrolyze cAMP and/or cGMP and release the product AMP and/or GMP. The potency of PDE inhibition by test compounds is determined with a commercially available in vitro enzymatic assay (IMAP® Fluorescence Polarization assay, Molecular Devices Corp.). Fluorescently labeled cAMP or cGMP is hydrolyzed by PDE preparations and in a second step, binding of labeled product to a large binding partner allows product detection by fluorescence polarization (FP) measurements. Stock solutions of the test compounds are made in DMSO and diluted in assay buffer (10 mM Tris-HCl, 10 mM $MgCl_2$, 0.1% BSA 0.05% $NaN_3$, pH 7.2) to the desired concentrations. The solutions used in the assay contain the test compound in assay buffer with 2% DMSO. 5 μl of this pre-diluted test compound solution are mixed with 10 μl of substrate (FL-cAMP or FL-cGMP) at concentrations recommended by the manufacturer and with 5 μl of appropriately diluted PDE. 5 μl of reaction buffer with 2% DMSO are used for control reactions. The final concentration of DMSO in the assay is 0.5%, which does not significantly alter the PDE activity. After incubation for 90 minutes at room temperature, 60 μl of binding reagent are added as specified by the manufacturer. Binding is allowed to proceed for 30 minutes and fluorescence polarization is measured. Dose dependence of PDE inhibition is measured by assaying dilution series of test compounds. $IC_{50}$ values are determined from the measured activities by curve fitting.

MIC Determination:

All MIC values are determined by broth microdilution according to the guidelines by the Clinical and Laboratory Standards Institute (CLSI, Wayne Pa., USA). *Staphylococcus aureus* ATCC29213 is grown on Müller-Hinton agar (MHA) (Becton Dickinson) and then in cation-adjusted Müller Hinton broth (CaMHB) (Becton Dickinson) for 24 h at 37° C. *Streptococcus pyogenes* ATCC19615 and *Moraxella catharrhalis* QK34 are grown on MHA with 2.5% Laked Horse Blood (Oxoid). Liquid cultures in CaMHB+ 5% horse serum (Sigma) are incubated for 24 h at 35° C. in a 5% $CO_2$ atmosphere. *Haemophilus. influenzae* 3168 is grown on MHA+2.5% Fildes extract (Oxoid). Liquid cultures are grown in CaMHB+5% Fildes extract at 35° C. in a 5% $CO_2$ atmosphere. Propionibacteria are grown on Wilkins-Chalgren agar (WCA) (Oxoid) for 72 h under anaerobic conditions. Liquid cultures are grown anaerobically in Wilkins-Chalgren broth (WCB) (Oxoid) for 48 h at 35° C. MIC values are obtained by broth microdilution using WCB (Anaerobe Broth MIC, Difco). Microtitre plates are loaded into 7-L GENbox anaerobic incubation jars (BioMerieux) fitted with anaerobic atmosphere generators (BioMerieux) and a Dry Anaerobic Indicator Strip (BBL). Under these conditions, an $O_2$ concentration<0.1% is achieved by 2.5 h, and a $CO_2$ concentration>15% by 24 h. MIC values are read after incubation at 35-37° C. for 48 h.

Oral Bioavailability:

Drug concentrations in blood or plasma are determined as a function of time in pharmacokinetic studies. Mice were treated with the test compound at defined doses. 10 mg/kg is used for oral administration and 1 mg/kg is taken for intravenous administration. Blood or plasma samples are collected at defined time-points and the drug content is determined by LC-MS/MS. The drug concentration is plotted as a function of time and the non-intravenous (oral) and the intravenous area under the curve (AUC) is calculated using the linear trapezoidal rule. The oral bioavailability is then calculated using dose-normalized AUC with the following formula:

$$F[\%]=AUC_{oral}/AUC_{intravenous}*100$$

Blocking of hERG Channel:

The whole-cell patch clamp technique is used to measure the effect of test compounds on hERG tail currents from stably transfected HEK 293 cells (B'SYS GmbH, CH-4108 Witterswil, Switzerland). 0.1% DMSO is used as vehicle and the system is validated with 10 nM of the selective $I_{Kr}$ blocker E-4031.

Cells are grown in culture flasks at 37° C. in a humidified atmosphere with 5% $CO_2$ and are passaged when 50-80% are confluent. The culture medium is a 1:1 mix of Dulbecco's modified eagle medium and nutrient mixture F-12 (D-MEM/F-12 1×, with L-Glutamine) supplemented with 9% foetal bovine serum and 0.9% penicillin/streptomycin solution. For electrophysiological measurements, cells are seeded into 35 mm sterile culture dishes containing 2 ml of culture medium with antibiotics (complete medium was supplemented with 100 μg/ml hygromicin B and 15 μg/ml blasticidin). Cells are cultivated at a density allowing single cells to be measured in order to avoid uncertainties due to electrically coupled cells (Pritchett et al. 1988, Verdoorn et al. 1990). DMSO stock solutions of test compounds are appropriately diluted with bath solution (10 mM HEPES pH 7.4, 137 mM NaCl, 4 mM KCl, 1.8 mM $CaCl_2$, 1 mM $MgCl_2$, 10 mM D-Glucose). Pipette solution (10 mM HEPES pH 7.2, 130 mM KCl, 1 mM $MgCl_2$, 5 mM Mg-ATP, 5 mM EGTA.) was prepared and stored as frozen aliquots between −10° C. and −30° C.

The 35 mm culture dishes are placed under the microscope and continuously perfused with bath solution at approximately 1 ml/min. All solutions applied to cells including the pipette solution are maintained at room temperature (19° C.-30° C.). After formation of a Gigaohm seal between the patch electrodes and an individual cell (pipette resistance range: 2.0 MW-7.0 MW; seal resistance range: >1 GW) the cell membrane across the pipette tip is ruptured to assure electrical access to the cell interior (whole-cell patch-configuration). As soon as a stable seal is established, hERG outward tail currents are measured upon depolarization of the cell membrane to +20 mV for 2 s (activation of channels) from a holding potential of −80 mV and upon subsequent repolarization to −40 mV for 3 s. This voltage protocol is run at least 10 times at intervals of 10 s. If the current density is too low for measurements, another cell is analyzed. Once control recordings are accomplished, cells are continuously perfused with bath solution containing a test compound. During wash-in of the test compound the voltage protocol is run continuously at 10 s intervals until the steady-state level of block is reached.

Values (in pA/nA) of the peak amplitudes of outward tail currents are generated for each voltage step and printed for compilation and analysis. The recorded current amplitudes at the steady state level of current inhibition are compared to amplitudes from control conditions measured in the pre-treatment phase of the same cell. The current block is calculated as percentage of control. To determine whether the observed current inhibition is due to a test item interaction with the hERG channel or due to current rundown, these residual currents are compared to those measured in vehicle treated cells. Mean values are calculated for each compound with data from at least 2 individual cells.

The invention claimed is:

1. A method for treating a disease or disorder by inhibiting phosphodiesterase 4 in a subject in need thereof, comprising the step of administering a therapeutically effective amount of a compound according to formula (1):

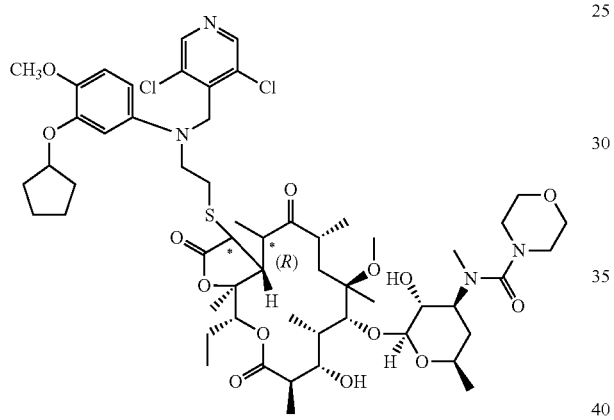

(I)

or a pharmaceutically acceptable salt or ester thereof, wherein * indicates a stereocenter which is in (R) or (S) configuration.

2. The method according to claim 1, wherein the compound of formula (I) is of formula (I-A):

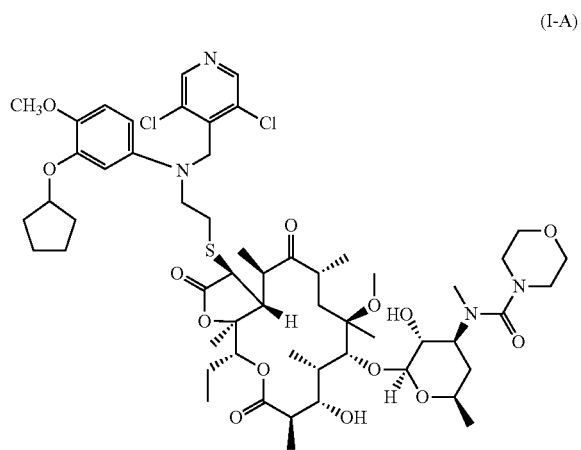

(I-A)

or a pharmaceutically acceptable salt or ester thereof.

* * * * *